United States Patent [19]

von Philipp et al.

[11] Patent Number: 4,526,320

[45] Date of Patent: Jul. 2, 1985

[54] APPARATUS FOR VAPORIZING INSECTICIDES, PERFUMES AND/OR OTHER VOLATILE AGENTS

[75] Inventors: Fritz von Philipp, Neuburg; Georg Schimanski, Hagen, both of Fed. Rep. of Germany

[73] Assignee: Globol-Werk GmbH, Nuremberg, Fed. Rep. of Germany

[21] Appl. No.: 491,213

[22] Filed: May 3, 1983

[30] Foreign Application Priority Data

May 15, 1982 [DE] Fed. Rep. of Germany ....... 3218480
May 15, 1982 [DE] Fed. Rep. of Germany ....... 3218481
May 15, 1982 [DE] Fed. Rep. of Germany ... 8214314[U]

[51] Int. Cl.³ .............................................. A61L 9/04
[52] U.S. Cl. ....................................... 239/43; 239/34; 239/44; 239/51.5; 239/57; 239/58
[58] Field of Search ...................... 239/34, 37, 43, 44, 239/45, 51.5, 58, 53–57; 222/81, 129, 135

[56] References Cited

U.S. PATENT DOCUMENTS

| 3,727,840 | 4/1973 | Nigro | 239/43 |
| 4,161,284 | 7/1979 | Rattan | 239/43 |
| 4,247,042 | 1/1981 | Schimanski et al. | 239/43 |
| 4,323,193 | 4/1982 | Compton et al. | 239/44 |

FOREIGN PATENT DOCUMENTS 274140 7/1927 United Kingdom ................ 239/44

Primary Examiner—Andres Kashnikow
Assistant Examiner—James R. Moon, Jr.

[57] ABSTRACT

Evaporator device for insecticides, perfumes and/or other volatile substances, having a housing containing ports, which has at least one receiving section in which a container for the active substances is inserted, and at least one opener associated with the container, while relative movement between the container and the opener can be performed for the opening of the container, and also, if desired, an element absorbing the active substances emerging from the container, an opening being provided in the casing (1,2) in the area of each receiving section (7), through which at least a portion of the wall (8) of the container (4) inserted in the receiving section (7) is exposed to the exterior.

9 Claims, 9 Drawing Figures

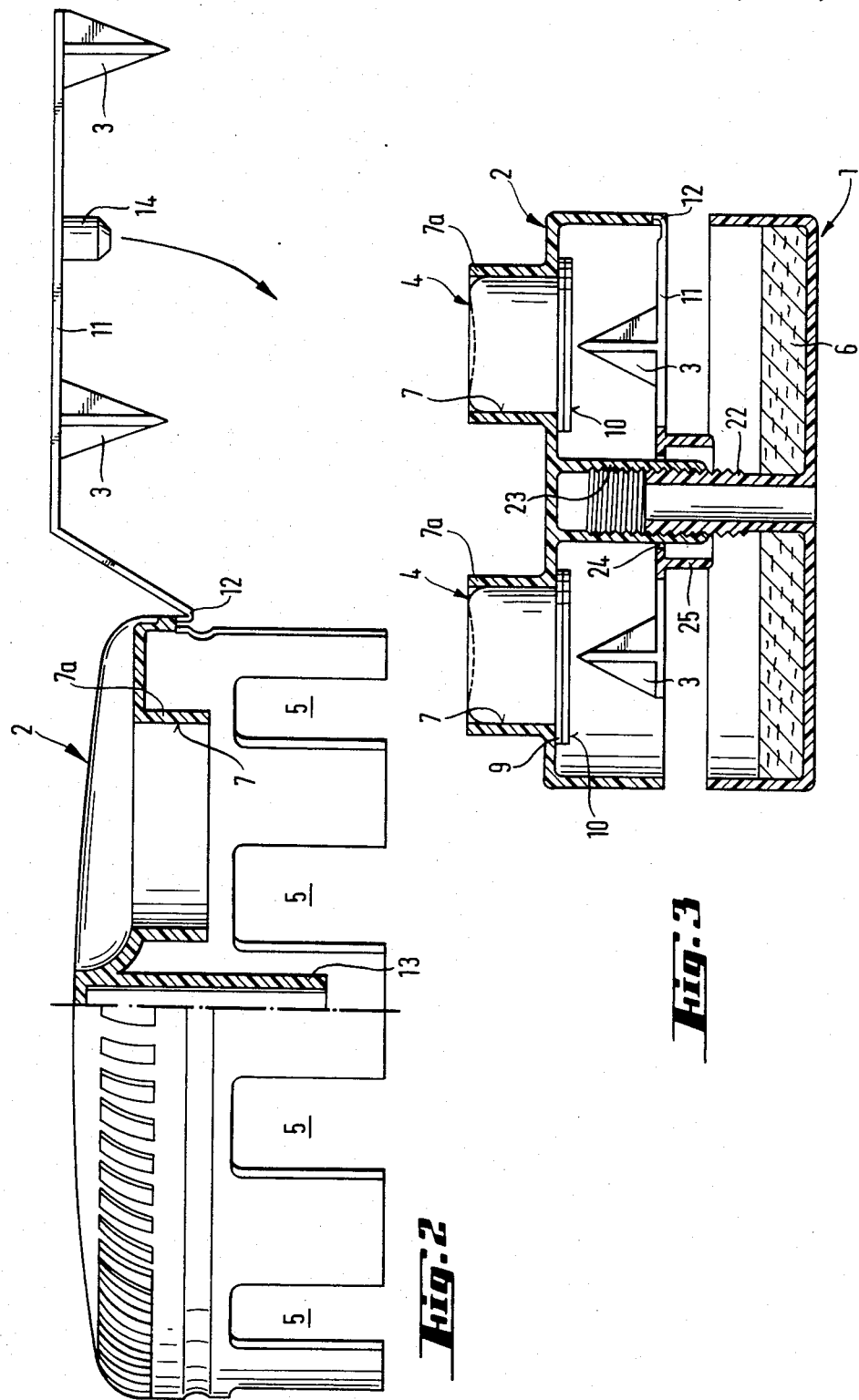

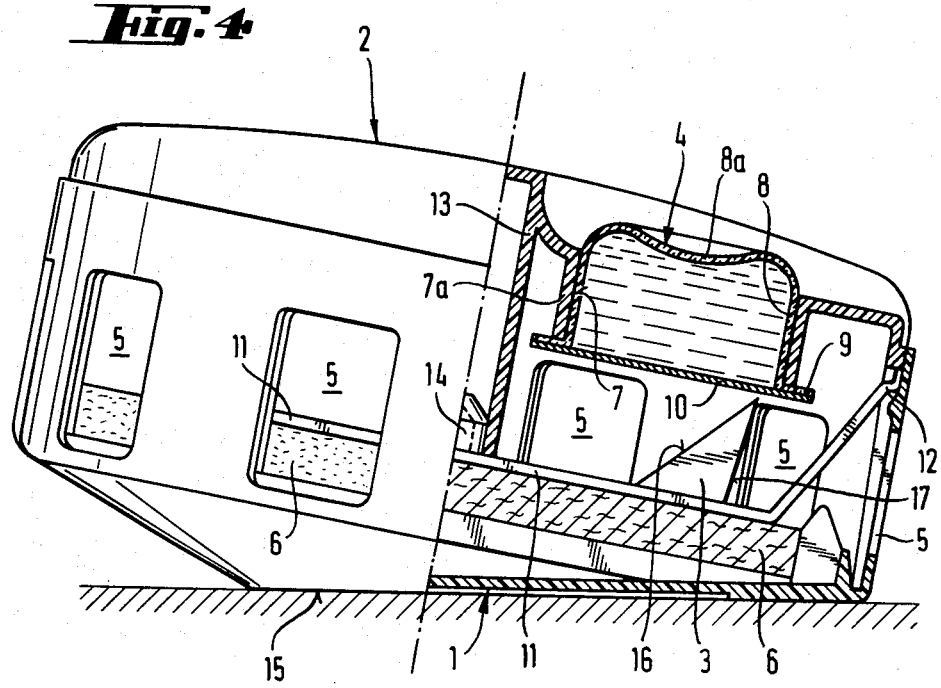
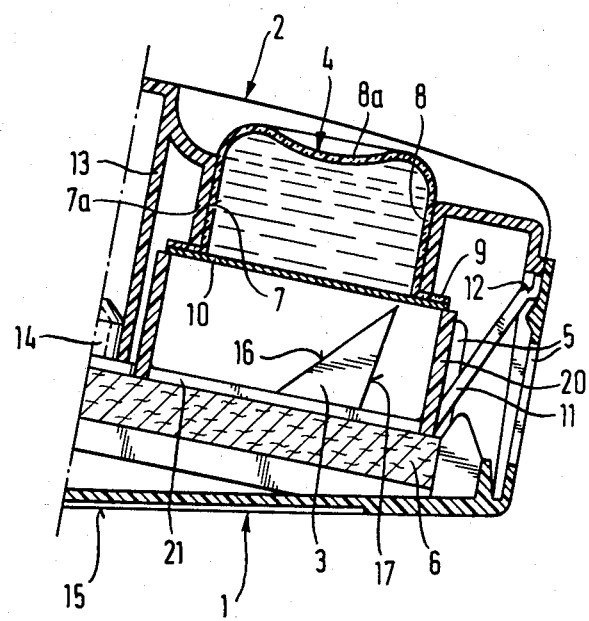

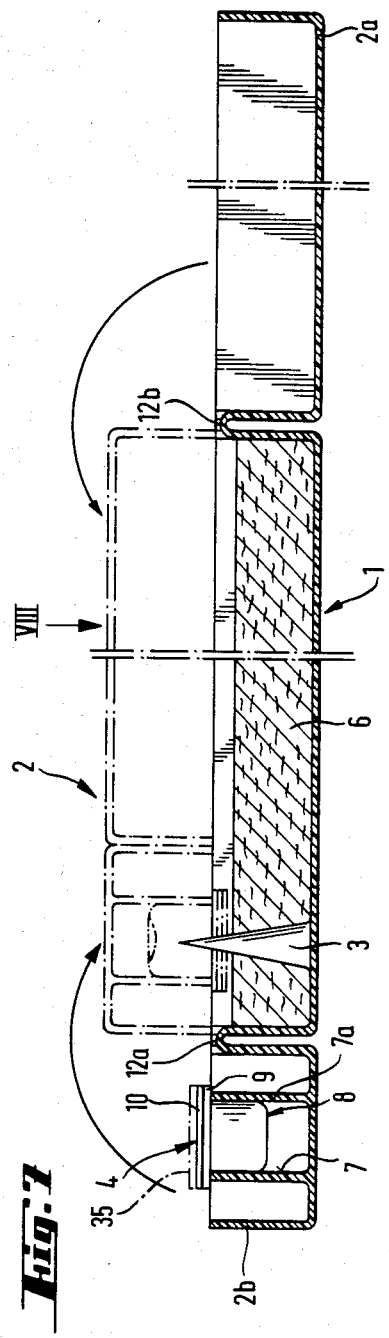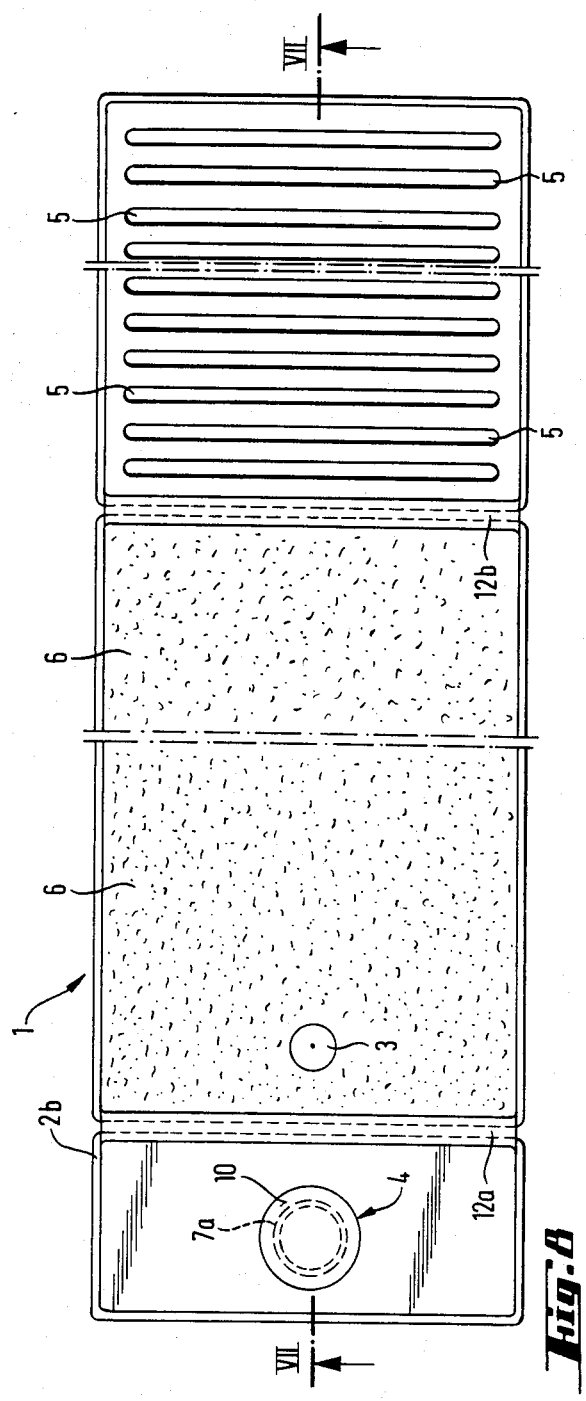

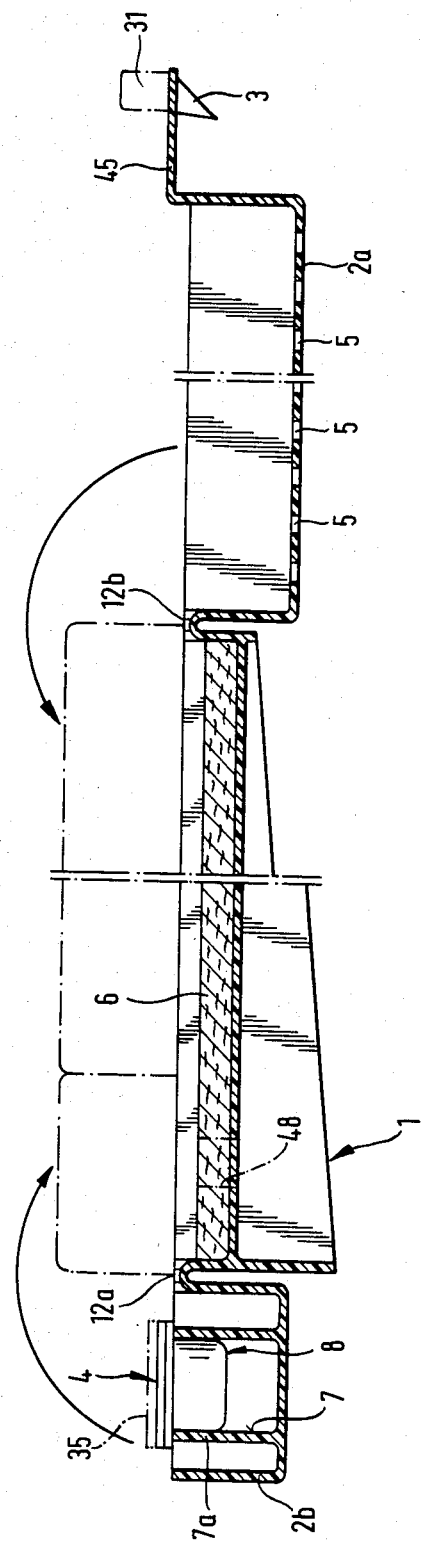

APPARATUS FOR VAPORIZING INSECTICIDES, PERFUMES AND/OR OTHER VOLATILE AGENTS

BACKGROUND OF THE INVENTION

The invention relates to a device for the evaporation of insecticides, perfumes and/or other volatile agents, the device having a housing containing ports, at least one receiving section in which a container for the active substances is inserted, and at least one opener means associated with the container, while relative movement between the container and the opener means can be performed for the opening of the container.

An evaporator device of the kind specified above is already known from German Pat. No. 2,807,424 corresponding U.S. Pat. No. 4,247,042 to Schimanski et al. This evaporator device makes possible the use of only one cartridge of active agents. The cartridge of the agent has to be opened by exerting a pressure on it for the purpose of piercing it. If the cartridge is made of resilient material, it is possible that the opening thus made might reclose due to the re-forming of the material, thus preventing the continuous escape of all of the active agent.

BRIEF SUMMARY OF THE INVENTION

It is the object of the invention, however, to improve an evaporator in accordance with the foregoing so as to simplify the replacement of the cartridge while at the same time providing for the opening of the cartridge in a simple and reliable manner. This object is accomplished in accordance with the invention by the device hereinafter more fully described.

The invention provides an evaporator device in which more than one cartridge for active agents can be used. Thus it is possible, after the active agents of one cartridge are used up, to open the next cartridge to release its agents. The opening of the cartridge itself is accomplished simply by either pushing it against its associated opener means, or by displacing one of the opener means toward the corresponding cartridge for the purpose of piercing the latter.

To replace empty cartridges, the evaporator box is opened in a simple manner; replacement of empty cartridges with full cartridges enables the evaporator device to be reused over a long period of time.

While in one embodiment of the evaporator device an element for the absorption of the active agents is disposed within the side of the box remote from the cartridges and opener means, in another embodiment this element, in the form, for example, of a plurality of individual layers, is disposed between the cartridges on the one hand and the opener means on the other, these layers being disposed preferably on the container surface confronting the opener units.

In another embodiment, the cartridge containing the active agents is transparent at a portion of its wall which is exposed within openings in the casing; this makes it possible to determine easily whether the cartridge in question is full of the agent, partially full, or empty.

In another embodiment, the surface or wall of the cartridge facing the opener means is made shallow or planar and consists of a perforable foil or film, while the rest of the cartridge wall is made of a material that is stiffer and more resilient than the perforable film. In a preferred embodiment, the cartridge is cup-shaped, while its surface facing the opener means is planar and consists of perforable material; the cup-like portion of the cartridge can be transparent or pigmented.

In a preferred embodiment, the piercing of the perforable film by the opener means is accomplished by pressing the preferably cup-shaped cartridge with the fingers against the opener units, and the sharp-tipped or spur-like elements of the opener means penetrate the perforable foil or film. In another embodiment, openings are also provided on the back of the box, through which opener means can be actuated such that their spur-like elements penetrate the cartridge, the cartridges in this case being held fixedly in the box.

Advantageously, all parts of the box can be manufactured in common in a single working operation. The evaporator device can be assembled in a simple and nonhazardous manner: after first inserting the active agent cartridges, the parts of the casing are folded together and the evaporator device is ready to operate.

BRIEF DESCRIPTION OF THE DRAWING

Preferred embodiments of the evaporator device will now be described in conjunction with the drawing for the purpose of explaining additional features.

FIG. 2 is a perspective view, partially in cross section, the evaporator device of FIG. 1, FIG. 3 is a cross section of a second embodiment of the evaporator device, FIG. 4 is another embodiment of an evaporator device, partially in cross section, FIG. 5 is a fragmentary cross section of the evaporator device of FIG. 4, FIG. 7 is a cross section of another embodiment of the evaporator device, FIG. 8 is a plan view of the embodiment of FIG. 7, and FIG. 9 is a diagrammatic cross-sectional representation of a variant of the embodiment represented in FIG. 7.

DETAILED DESCRIPTION OF PREFERRED EMBODIMENTS

Figure 1:
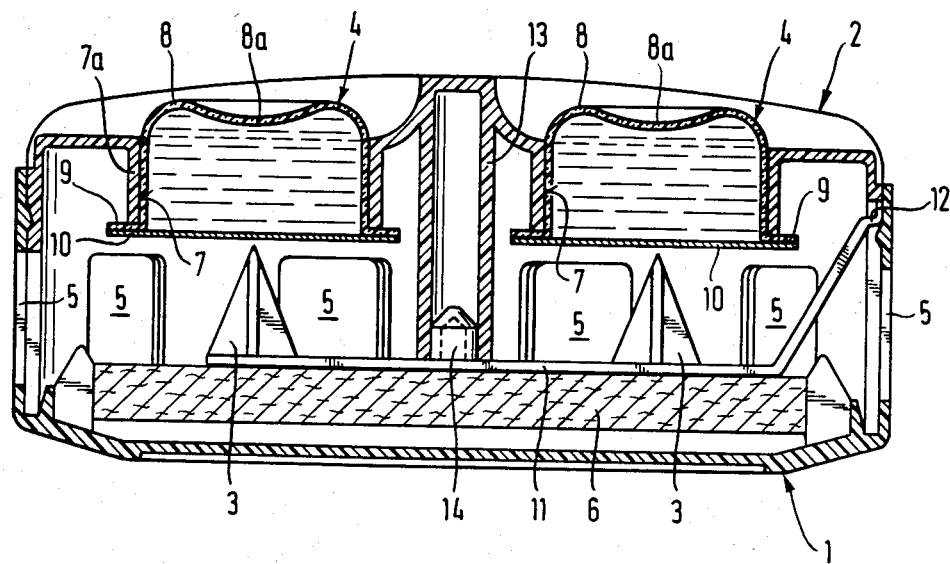
FIG. 1 is a cross-sectional view of a first embodiment of the evaporator device.

The evaporator device described hereinafter in conjunction with FIGS. 1 to 9 has in each case a box consisting of a dish-like bottom part 1, and an upper part 2 capping the bottom part 1. In the box there is provided an opener means 3 and at least one cartridge 4 containing volatile agents, such as insecticides, for example. The box parts 1 and 2 are made by molding, preferably from plastic, in a simple mold consisting of an upper part and a lower part. The box parts 1 and 2 are assembled so as to be rotatable against one another about a vertical axis, so that by turning the upper box part 2 against the lower part 1 the openings or ports 5 disposed in the box periphery can be opened or closed to a greater or lesser extent. The ports 5 enable the active agents flowing from the cartridge or cartridges 4 within the box to escape to the surrounding atmosphere. The evaporating device has an absorbent element 6 which consists preferably of cellulose and serves to absorb active agents emerging from the cartridge 4 and hold them such that the substances can gradually be released to the atmosphere through the ports 5. Preferably, the element 6 absorbing the active agents is disposed in the lower part 1 of the box, as illustrated in FIG. 1. In the upper part 2 of the box there are provided a plurality of cylindrical chambers 7 disposed about the axis of rotation of the box and parallel thereto. These openings serve to accommodate the cartridge or cartridges 4, a cartridge being inserted into each from the lower side of the upper part of the box. The active agent cartridge consists preferably of a cup 8 made, for example, of a transparent material such as plastic, or of a pigmented film. The cup 8 has a flange 9 and a bottom 10 hermetically sealed to the flange 9 and consisting of a perforable material, preferably a metal foil, which forms the surface of cartridge 4 that faces the corresponding opener means 3. The bottom 10 is preferably of planar shape. The chambers 7 for each cartridge 4 are constituted, in the embodiment shown in FIGS. 1 and 3, by sleeves 7a which are aligned approximately parallel with the casing axis, as represented in the embodiments shown in FIGS. 1 and 3. The diameter of the preferably cylindrical sleeve 7a is slightly greater than the corresponding outside diameter of the cartridge 8 inserted into the chamber 7, the flange 9 of each cartridge 4 having a diameter that is larger than the diameter of the sleeve 7a, so that each cartridge 4 is held by its flange 9 within the opening 7.

Underneath each chamber 7 and therefore underneath each cartridge 4 there is disposed an opener 3 which is formed of at least one spur-like element. The opener means 3 are formed on a common strip-like support 11 disposed across the diameter of the casing, one end of the support 11 being attached by means of a film hinge 12 or the like to the upper box part 2. As shown in FIGS. 1 and 2, the support 11 bearing the opener means 3 is made extending radially from the upper part of the casing, so that the molding of the upper part 2 and support 11 can be performed integrally in only one two-part mold.

In the embodiment shown in FIG. 1, a tube 13 extends downward toward the bottom part 1 of the box concentrically with the box axis or axis of rotation, and it is engaged at least with a friction fit by a stud 14 projecting from the support 11 such that the support comes to rest against the mouth of the tube 13. The support 11 can be secured in the position of use also by snap fastening means formed thereon. Instead of a single spur-like element forming each a single opener 3, a plurality of such elements can be provided for a single container 4, each group of such spur-like elements being held by the support 11 underneath the cartridge 4 in the box, in the manner described. In a preferred embodiment, each element of each opener unit 3 terminates in a chisel tip.

In the evaporator device of FIG. 3, the upper part 2 of the box is made so as to be removable from the bottom part 1 by means of a centrally disposed screw, so that the casing can be opened to a greater or lesser degree. For this purpose, a hollow threaded stud 22 projects from box part 1, and an internally threaded sleeve 23 from the upper part 2. The support 11 has a bore 24 which is engaged with clearance by the internally threaded sleeve 23. Coaxially with the bore 24, a nipple 25 is formed on the support 11 and comes to rest against the absorbing element 6.

The cartridges 4 are inserted into the socket 7a from the inside of the upper part 2 of the box. It can be seen that either just one cartridge 4, or two or more such cartridges, can be inserted into the evaporator device of the invention, and they can also be arranged eccentrically if desired. To open the cartridge 4, the cartridge has to be displaced manually out of the chamber 7 against the corresponding opener means 3, until the point of the associated opener or spur 3 penetrates the bottom 10 formed preferably by a perforable foil or film, so that the active agents in the cartridge 4 will emerge and trickle down onto the absorbent element 6 contained in the bottom part 1 of the box. The absorbent element 6, in the form of a layer of cellulose, for example, absorbs the active substances and permits a gradual evaporation of same into the atmosphere. The use of a perforable foil or film as the bottom 10 of cartridge container has the advantage that the active substances emerge completely from the cartridge after the bottom 10 has been pierced, and prevents the reclosing of the puncture or punctures formed by the opener 3, after the pressure of, for example, a finger on the cartridge has been removed. This assures the complete emptying of each cartridge 4. If the cup-like part 8 of the cartridge is made of a transparent material, it is possible for the user of the evaporating device to determine by visual inspection the level of the agent in each cartridge 4 and, in case of necessity, to pierce the still-full cartridges in the manner described so as to release the substances contained therein. Since the cartridges 4 have to be displaced with the finger out of the chamber 7 toward the associated opener unit 3, and then pressure must be exerted on them to pierce the bottom 10, the material selected for the cup-like body 8 must be one whose strength is sufficient to prevent damage to the cup 8 when its bottom is pierced. As it appears from the above description, only the bottom 10 is to be perforated by the spurs or opener means 3, but the remainder of each cartridge 4 is to be highly resistant to deformation and must withstand the forces exerted on it for the purpose of piercing it. This means that the cup 8 of the cartridge must be more resistant to deformation than the foil or film forming the bottom, which is penetrable by the corresponding opener means 3, to such a degree that the pressing force necessary for the piercing of the film or foil can be transmitted by the cup 8 alone.

In FIGS. 4 and 5 are shown additional embodiments of the evaporator means for insecticides, perfumes and/or other volatile substances. In these embodiments, one spur-like element is mounted on the support 11 for each cartridge 4. The support 11 can be secured in the active position by snap-fastening elements formed thereon. The box has a bottom part 1 having an inclined base 15, while the absorbent element 6, the support 11 and the bottom 10 are in a substantially parallel arrangement, as seen previously in FIGS. 1 to 3. The support 11 bears as the opening means 3 one spur-like element for each, the point of this spur-like element being located adjacent to the flange 9, and each spur-like element having a cutting edge 16 directed away from the rim 9 and another edge 17. The piercing of the cartridge represented on the right in FIG. 4 is performed in the same manner as has been described above, namely by exerting a pressure on the cartridge 4 by a finger, moving the cartridge against the corresponding opener means 13, so that the tip of the opener 13 perforates the bottom 10 and permits the escape of the substance from the cartridge 4; consequently, the substances flow out of the cartridge and are absorbed by the absorbent element 6. To facilitate the piercing, and especially to prevent each cartridge from rocking as it is pressed against its opener 3, the cup 8 is provided with a dome 8a so that the cartridge can be pressed securely into the box or evaporator with a finger of one hand; the dome 8a furthermore stiffens the cartridge 4 such that the force necessary for the perforation of the film or foil forming the bottom 10 can be exercised directly through the cartridge 4.

In the embodiment represented in FIG. 5, there is associated with each cartridge 4 of the type of construction described in conjunction with FIGS. 1 to 4, a cylindrical body 20 whose bottom is in intimate contact with the absorbent element 6, and which is made integral with the support 11. A bridge 6 is formed integrally with the cylindrical body 20 across the diameter thereof, and on it the opener unit 3 is formed within the cylinder 20. The inside diameter of the cylindrical body 20 is slightly smaller than the outside diameter of the bottom 10 formed by the foil or film on the cartridge 4, and greater than the diameter of the cylindrical chamber 7. The height of the opener means 3 is less than the height of the cylindrical body 20, i.e., the opener means 3, or the spur-like element 3 forming the opener means 16, does not extend beyond the cylinder 20, so that, when the cartridge 4 is pushed into the box for the purpose of piercing the bottom, the film forming the bottom sealingly engages the cylindrical body 20 over its entire circumference within the latter, and only then is it penetrated or pierced by the opener unit 3. This assures that the substance emerging from the cartridge 4 will not escape laterally into the upper part or lower part of the box, as would be possible in the case of the embodiments shown in FIGS. 1 to 4 if the evaporator device were tilted, and instead it is guided by the cylinder 20 to the absorbent element 6. By setting the opener means 3 at a distance from the cylinder 20, the assurance is given that the film or foil forming the bottom 10 of the cartridge 4 will not be perforated by the opener means 3 until the flange 9 of the bottom 10 is in tight contact with the cylinder 20 and thus the active substances cannot bypass the cylinder to enter the box, but are guided towards the absorbent element.

In the embodiment shown in FIG. 5, the application of force by a finger on the dome 8a or on the wall of the cup 8 extending out of the corresponding socket 7 brings it about that the bottom 10 will bulge more or less greatly toward the opener means 3, causing it to be pierced by the latter. The distance that can be seen in FIG. 5 between the bottom 10 and the opener means 3 is reduced by the force exerted on the cartridge 4 to such an extent that the tip of the opener means 3 penetrates the bottom 10.

Figure 6:
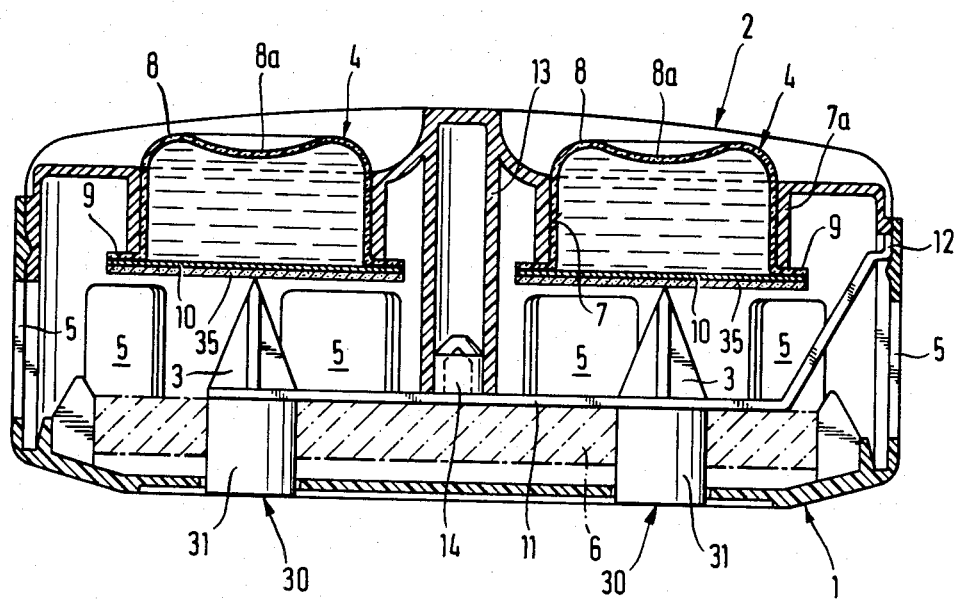
FIG. 6 is a cross-sectional view of another embodiment of an evaporator device.

An additional embodiment of the evaporator device will now be described in conjunction with FIG. 6. This embodiment is of substantially the same construction as shown in FIGS. 1 to 5, but in this case it is not the cartridge 4 that is pushed toward the corresponding opener means 3 to open the film or foil bottom 10. Instead, each opener means 3 can be operated through a corresponding opening 30 formed in the bottom part 1 of the box such that the tip of the opener 3 can be moved against the bottom 10 of the cartridge 4. Each chamber 7 is constructed in the same manner as described in conjunction with FIG. 1, while the opener means 3 differs from the one represented in FIG. 1 in that each sharp-tipped element, which is part of the opener or forms the opener means, has a prolongation 31 extending away from the inserted cartridge and coming to lie within the corresponding aperture 30 formed in the bottom part 1 of the box. Thus, each individual opener means 3 can be pushed with the finger against the cartridge 4. The opener means are in this case fastened to the support 11 in the same manner as described above, but the support 11 must have a certain elasticity to permit the individual opener means 3 to be pushed independently of one another against the cartridge 4. In the embodiment represented in FIG. 6, the absorbent element can be provided in the form of a sheet laid in the bottom part 1 of the box as described in conjunction with that figure, the sheet that forms the absorbent element 6 then having to be provided with openings to accommodate the prolongations 31.

Thus, the element 6 is provided in the same manner as in the embodiment shown in FIG. 1, but it has a plurality of openings corresponding to the cross-sectional area of the prolongations 31, so that the prolongations will be able to extend from the opener means 3 toward the bottom part 1 of the housing, through the absorbent element 6, to the opening 30 in the casing bottom 1, and thus can be operated from the outside for the opening of the bottom 10 of any particular cartridge 4. The element 6 is represented in broken lines in FIG. 6. In another embodiment, the absorbent element 6 is not provided in an evaporator device in accordance with FIG. 6, and instead the face of the bottom 10 of each cartridge is provided with a relatively thin covering 35 which has an absorbency comparable to the absorbency of the element 6. The covering 35 has such a thickness that perforation of the bottom 1 by the opener units 3 is assured and reclosing of the perforation by the covering 35 itself is prevented. In this embodiment, the assurance is given that the substance emerging from the cartridge 4 will pass through the perforation made by the corresponding opener means 3 and enter into the absorbent covering 35 for evaporation, and as a result of the direct contact between the covering 35 and the substance in cartridge 4, the covering 35 will continuously absorb substance from the cartridge 4 through the perforation in bottom 10 produced by the opener means 3, and release it for evaporation into the atmosphere.

Another modified embodiment of the evaporator device is described hereinafter in conjunction with FIGS. 7 to 9. In this embodiment, the box consists of a bottom part 1 and a divided upper part, the one division being designated as 2a and the other one, containing the socket 7 for the cartridge 4, as 2b. The two upper part divisions 2a and 2b are hinged to edges on opposite sides of the bottom part 1 of the casing, preferably by film hinges 12a and 12b, as indicated in FIG. 7, the left hinge 12a therein serving to fasten upper part division 2b to the bottom part 1 of the casing, and the right hinge 12b serving for the articulation of division 2a to the bottom part 1 of the casing. The chamber 7 consists, as in the embodiments described above, of cylindrical sleeves 7a, which, in the case of largely cylindrical cups 8, are also of cylindrical shape, the inside diameter of sleeve 7a being slightly greater than the outside diameter of the cup 8. The cartridges 4 have substantially the same form as described in conjunction with FIGS. 1 to 6, i.e., they have a flange 9 extending over the sleeve 7a and serving as an abutment against movement of the cartridge 4 from the chamber 7 towards the exterior of the box. The corresponding opener means 3 are formed in the bottom 1 of the box, and cause the perforation of the bottom 10 of cartridge 4 as soon as the box is closed, i.e., after the two box parts 2a and 2b are folded against the bottom part 1 of the box, and the particular cartridge 4 within the chamber 7 is pressed downwardly against the opener means 3. For the opening or perforation of each cartridge 4, substantially the same procedure is to be performed as explained in conjunction with FIG. 1. As it can be seen in FIG. 7, the bottom part 1 of the box contains the absorbent element 6 in the form of a sheet, having an opening to correspond to the opening means 3; if element 6 is of a relatively loose material, it is unnecessary to provide an opening for the opener means 3, and instead the element 6 is placed over the opener means provided in the bottom part of the box, in the form of a spur-like element 3, whereupon the element 3 will penetrate the element 6 and assume the position indicated in FIG. 7. As described in conjunction with FIG. 6, a cartridge 4 can be provided with an absorbent sheet 35 formed on its bottom, in which case the element 6 shown in FIG. 7 is eliminated. When the upper parts 2a and 2b of the box have been folded to the position represented in broken lines in FIG. 7, they will preferably snap onto the bottom part 1 by means of catches, which are not shown, provided on the bottom part 1, so that fortuitous and unintentional folding over of the upper parts 2a and 2b is prevented. The evaporation of the substance that has flowed into the absorbent element 6 or been absorbed by the sheet 35 is assured by the ports 5, which are formed preferably in the upper part 2a of the box and, if desired, can also be formed additionally in the upper part 2b thereof. A top view of the closed evaporator corresponding to the arrangement shown in solid lines in FIG. 7, is shown in FIG. 8. Instead of a single cartridge 4, two or more such cartridges and a corresponding number of chambers 7 can also be provided in this embodiment.

A modified embodiment of the device shown in FIG. 7 is shown in FIG. 9. In this embodiment the opener means 3 is formed, not in the bottom part 1 of the box, but, as represented in FIG. 9, in the upper part 2a thereof. The opener means is constituted by a tab 45. In the folded state shown in FIG. 9, this tab extends outwardly from the casing, and the opener means 3 in the form of a spur-like element projects substantially downwardly. When the upper part 2a of the case is turned to the position for use, as represented in broken lines in FIG. 7, then the upper part 2b of the casing is also folded to the position of use, as represented also in FIG. 7 in broken lines, the opener unit 3 comes to lie beneath the cartridge 4 and the latter can be pressed against the opener unit 3 for perforation of the bottom, by exerting a force on its cup 8. In this embodiment, too, the absorbent element 6 can be dispensed with if a cartridge 4 is used on whose bottom 10 an absorbent covering 35 is disposed. Lastly, in the embodiment shown in FIG. 9, the opener means can be provided with a prolongation 31 opposite the spur-like element, so that, after the upper part 2a has been folded from the position shown in FIG. 9 to the position shown in FIG. 7, the prolongation 31 will come to rest in an opening 48 provided therefor and represented in broken lines in FIG. 9. Thus, each cartridge 4 can be pierced by actuating the opener means through the opening 48 in the floor of the bottom part 1 of the box such that the spur-like element will be pressed into the bottom 10 of the particular cartridge 4, as was explained in conjunction with FIG. 6.

If a cylindrical body 20 is used in conjunction with the support 11, as described with reference to FIG. 5, and if an absorbent element 6 is used and inserted into the bottom part 1 of the box, the arrangement will be made such that the cylindrical body 20 will rest with its bottom edge largely on the element 6, so that, after the film or foil bottom 10 is pierced by the opener means 3, the assurance is had that the active substances will flow to element 6 and only to element 6. It is apparent that the cylindrical body 20 can be provided also in the embodiments shown in FIGS. 1 to 4 and 6 to 9, in order to prevent any lateral escape toward the inner wall of the casing of the substances emerging from the cartridge 4.

From the above description it is apparent that the evaporator can be designed for the accommodation of one or more cartridges of active substances--two for example. The use of a plurality of cartridges within an evaporating device has the advantage that the device can be left in the ready-for-use condition for a long period of time. The cup 8 can in this case be made of a transparent material so that one can readily see whether it is filled with the substance, or partially full or empty. On the other hand, the cup 8 can also be made of a pigmented film, in which case care must be taken to see that it has a greater stiffness than the bottom 10, also formed of a film, which seals the cup 8.

The cylindrical body 20, which is preferentially provided, has a height which is equal to or smaller or even greater than the height of the spur-like element or opener means 3. Advantageously, the height of the cylinder 20 is selected such that the flange 9 of the cartridge 4 will lie on the cylinder 20 before the bottom 10 is perforated, i.e., before the active substances emerge.

We claim:

1. An evaporator device for insecticides, perfumes and/or other volatile substances, having a housing containing ports, and having an upper part and a lower part which housing has a receiving section in said upper part and in which a perforable container for the volatile substances is inserted, at least one opener means in said lower part contactable with said container for perforation of same, said lower part being rotatable with respect to said upper part to cause said opener means to pierce said container located in said receiving section to cause opening of the container and release of said volatile substances, the surface of the container facing the opener means being substantially planar and comprising a perforable film or foil, the rest of the container being stiffer and more resilient, means for absorbing the volatile substances emerging from the container upon perforation thereof, said ports communicating said released volatile substances with the atmosphere, and a further opening provided in said housing in the area of the receiving section through which at least a portion of the wall of the container inserted into the receiving section is exposed to the exterior, a wall of the container facing away from the receiving section comprising transparent of pigmented material.

2. A device according to claim 1, wherein said container is displaceable within said receiving section toward a corresponding opener means.

3. A device according to claim 1, wherein said opener means is displaceable within said receiving section toward a corresponding container.

4. A device according to claim 1, wherein said container has a laterally projecting collar, the outside dimension of which is greater than that of said receiving section, said collar being confined within said housing when said container is inserted therein.

5. A device according to claim 1, wherein an annular body is provided in the area of said opener means.

6. A device according to claim 1, wherein said opener means has at least one spur-like element tapering toward the receiving section.

7. A device according to claim 1, wherein said absorbing means is disposed between said opener means and said container.

8. A device according to claim 1, wherein said absorbing means is formed by an absorbent layer disposed beneath said opener means.

9. An evaporator device for insecticides, perfumes and/or other volatile substances, having a housing containing ports, and having an upper part and a lower part which housing has a plurality of receiving sections in said upper part and in which perforable containers for the volatile substances are inserted, a plurality of opener means in said lower part, each being individually contactable with a corresponding container for perforation of same whereby relative movement betweeen each container and an associated opener means causes opening of the container and release of said volatile substances, the surface of each container facing the opener means being substantially planar and comprising a non-resilient perforable film or foil covering means for maintaining a torn area open once perforated, the rest of the container being stiffer and more resilient than said film or foil covering means, means for absorbing the volatile substances emerging from each container upon perforation thereof, said ports communicating said released volatile substances with the atmosphere, and a further opening provided in said housing in the area of each receiving section through which at least a portion of the wall of the container inserted into the receiving section is exposed to the exterior, a wall of the container facing away from the receiving section comprising transparent or pigmented material.

* * * * *

UNITED STATES PATENT AND TRADEMARK OFFICE
CERTIFICATE OF CORRECTION

PATENT NO. : 4,526,320
DATED : July 2, 1985
INVENTOR(S) : VON PHILIPP et al

It is certified that error appears in the above–identified patent and that said Letters Patent are hereby corrected as shown below:

On the title page:

[73] Assignee: GLOBOL-WERK GmbH
Neuburg
Federal Republic of Germany

Signed and Sealed this

Eleventh Day of March 1986

[SEAL]

Attest:

DONALD J. QUIGG

Attesting Officer

Commissioner of Patents and Trademarks